US00PP12506P2

(12) United States Plant Patent
Allamand et al.

(10) Patent No.: US PP12,506 P2
(45) Date of Patent: Apr. 2, 2002

(54) PHILODENDRON PLANT NAMED 'XANADU-II'

(75) Inventors: Randy L. Allamand, Lake Placid; David R. Lilly, Boynton Beach, both of FL (US)

(73) Assignee: Twyford International, Santa Paula, CA (US)

( * ) Notice: Subject to any disclaimer, the term of this patent is extended or adjusted under 35 U.S.C. 154(b) by 0 days.

(21) Appl. No.: 09/484,661

(22) Filed: Jan. 18, 2000

(51) Int. Cl.[7] ..... A01H 5/00
(52) U.S. Cl. ..... Plt./381

(58) Field of Search ..... Plt./381

*Primary Examiner*—Bruce R. Campell
*Assistant Examiner*—Michelle Kizilkaya
(74) *Attorney, Agent, or Firm*—C. A. Whealy

(57) ABSTRACT

A distinct cultivar of Philodendron plant named 'Xanadu-II', characterized by its dark green, glossy, deeply-lobed leaves; long petioles; and upright growth habit. The new Philodendron is derived from the cultivar Winterbourn, disclosed in U.S. Plant Pat. No. 7,030. The new Philodendron is distinguished from the cultivar Winterbourn by its larger and more deeply lobed leaves, and its taller and more upright growth habit. These differences are particularly evident in juvenile plants which have not attained reproductive maturity.

1 Drawing Sheet

BACKGROUND OF THE INVENTION

The present invention relates to a new and distinct cultivar of Philodendron plant, botanically known as *Philodendron selloum*, and hereinafter referred to by the cultivar name Xanadu-II.

The new Philodendron is a naturally-occurring whole plant mutation of the commercial *Philodendron selloum* cultivar Winterbourn, disclosed in U.S. Plant Pat. No. 7,030. This mutation was discovered and selected by the Inventors in July, 1994 as a single plant within a tissue-cultured planting of the parent cultivar in a controlled environment in Sebring, Fla.

Asexual propagation of the new cultivar by divisions in Sebring, Fla., has shown that the unique features of this new Philodendron plant are stable and reproduced true to type in successive generations of asexual propagation.

BRIEF SUMMARY OF THE INVENTION

The new Philodendron has not been observed under all possible environmental conditions. The phenotype may vary somewhat with variations in environment such as temperature, light intensity, and/or fertilizer rate, without, however, any variance in genotype.

The following traits have been repeatedly observed and are determined to be the unique characteristics of the cultivar Xanadu-II. These characteristics in combination distinguish 'Xanadu-II' as a new and distinct cultivar and distinguish it from the parent cultivar, Winterbourn:

1. Plants of the new Philodendron are taller than plants of the cultivar Winterbourn; this difference is particularly evident when the plants are juvenile, that is before the plants attain reproductive maturity.

2. Plants of the new Philodendron are more upright than plants of the cultivar Winterbourn.

3. Leaves of plants of the new Philodendron are larger and more deeply lobed than leaves of plants of the cultivar Winterbourn; this difference is particularly evident when the plants are juvenile, that is, before the plants attain reproductive maturity.

4. Plants of the new Philodendron have fewer branches than plants of the cultivar Winterbourn.

BRIEF DESCRIPTION OF THE PHOTOGRAPH

The accompanying colored photograph illustrates the overall appearance of the new Philodendron, showing the colors as true as it is reasonably possible to obtain in colored reproductions of this type. Colors in the photograph may differ slightly from the color values cited in the detailed botanical description which more accurately describe the actual colors of the new Philodendron. The photograph comprises a side perspective view of a typical plant of the cultivar Xanadu-II grown in the landscape about 16 months after planting a single 7-week old tissue culture-derived liner.

DETAILED BOTANICAL DESCRIPTION

In the following description, color references are made to The Royal Horticultural Society Colour Chart except where general terms of ordinary dictionary significance are used. The following observations and measurements describe rooted liners that were grown outdoors for about 18 months in Sebring, Fla., with day temperatures averaging 27° C., night temperatures averaging 13° C., and light levels about 1,500 to 2,000 foot candles.

Botanical classification: *Philodendron selloum* cultivar Xanadu-II.

Parentage: Naturally-occurring whole plant mutation of *Philodendron selloum* cultivar Winterbourn, disclosed in U.S. Plant Pat. No. 7,030.

Propagation:

*Method.*—By tissue culture or by divisions.

*Time to root tissue-cultured liners.*—About seven weeks.

*Rooting habit.*—Very thick, fleshy; typical of species.

*Pseudobulbs.*—Not observed.

Plant description:

*Plant size.*—Height: About 90 to 100 cm. Width or spread: About 160 to 180 cm.

*Growth habit.*—Stem is upright; about 5.5 to 6.7 cm in diameter. Leaves closely spaced without internodes, forming compact crowns with about 22 to 30 leaves per stem. Plants typically with 4 to 6 crowns.

*Crop time.*—From rooted liners, about 8 to 9 months are required to produce finished plants in 15-cm containers.

*Stem color.*—Browner than, but closest to 199A. Leaf scars, 196A.

*Stem length.*—About 12 to 20 cm from soil level to base of youngest leaf petioles.

*Foliage description.*—Arrangement: Alternate. Length: Largest leaves are about 30 to 35 cm; average-sized leaves are about 21 to 27 cm. Width: Largest leaves are about 23 to 27 cm; average-sized leaves are about 19 to 22 cm. Thickness: Moderate. Aspect: Undulate; leaf blade tilts upward from midrib and primary veins. Shape: Ovate. Margin: Pinnatifid; with about 9 pairs of lobes. Texture: Smooth, glabrous; glossy. Color: Newly expanded leaves, upper surface: Darker and greener than, but closest to 144A; midrib, 146C streaked with 178A at petiole; primary veins, 146C streaked with 178A at petiole. Newly expanded leaves, lower surface: 146B to 146C; midrib, 178B often with blotches of 145C; primary veins, 178B often with blotches of 145C. Mature leaves, upper surface: 137A; midrib, 146B flushed with 200B to 200C at petiole; primary veins, 146B flushed with 200B to 200C at petiole. Mature leaves, lower surface: 147B; midrib, 145B flushed with 178A to 178B at petiole; primary veins, 145B flushed with 178A to 178B at petiole. Midrib: Straight, thick; upper surface, recessed; lower surface, protruding. Primary veins: Upper surface, sunken; lower surface, protruding. Petiole (petiole of fourth expanded leaf from the apex): Aspect: Straight and upright; about 30 to 40° from vertical axis. Length: About 45 to 56 cm. Diameter, mid-section: About 1.1 to 1.5 cm. Color: 146C flushed with 200B to 200C near the junction with leaf base. Petiole sheath: Shape: Elongate. Size: About 7 cm by 1 cm. Texture, both surfaces: Smooth. Color, both surfaces: 146C; towards margin, 145C; tinged with 200C to 200D. Cataphylls: Shape: Triangular. Length: About 17 to 30 cm. Width: About 8 to 10 cm at the base. Texture, both surfaces: Smooth. Color: Outer surface: 146B; towards margin, 146C to 146D. Inner surface: 155B.

Inflorescence description: Typical of the species; not commercially significant. Flowering recurrent; spathe and spadices arranged on erect peduncles; inflorescences last about four weeks on the plant.

*Spathes.*—Shape: Roughly ovate with pointed apex. Length: About 12 cm. Width: About 3.5 cm. Texture, both surfaces: Smooth. Color: Outer surface: Dull dark red suffused with green towards the base and somewhat lighter towards the apex. Inner surface: Towards the base, pale pink; towards the apex, cream-colored. Spadix color: Apex, cream-colored; mid-section and base, pink. Peduncles: Dull olive green; smooth. Seed: Seed production has not been observed.

Disease resistance: Plants of the new Philodendron have not exhibited resistance to pathogens common to Philodendron.

It is claimed:

1. A new and distinct cultivar of Philodendron plant named 'Xanadu-II', as illustrated and described.

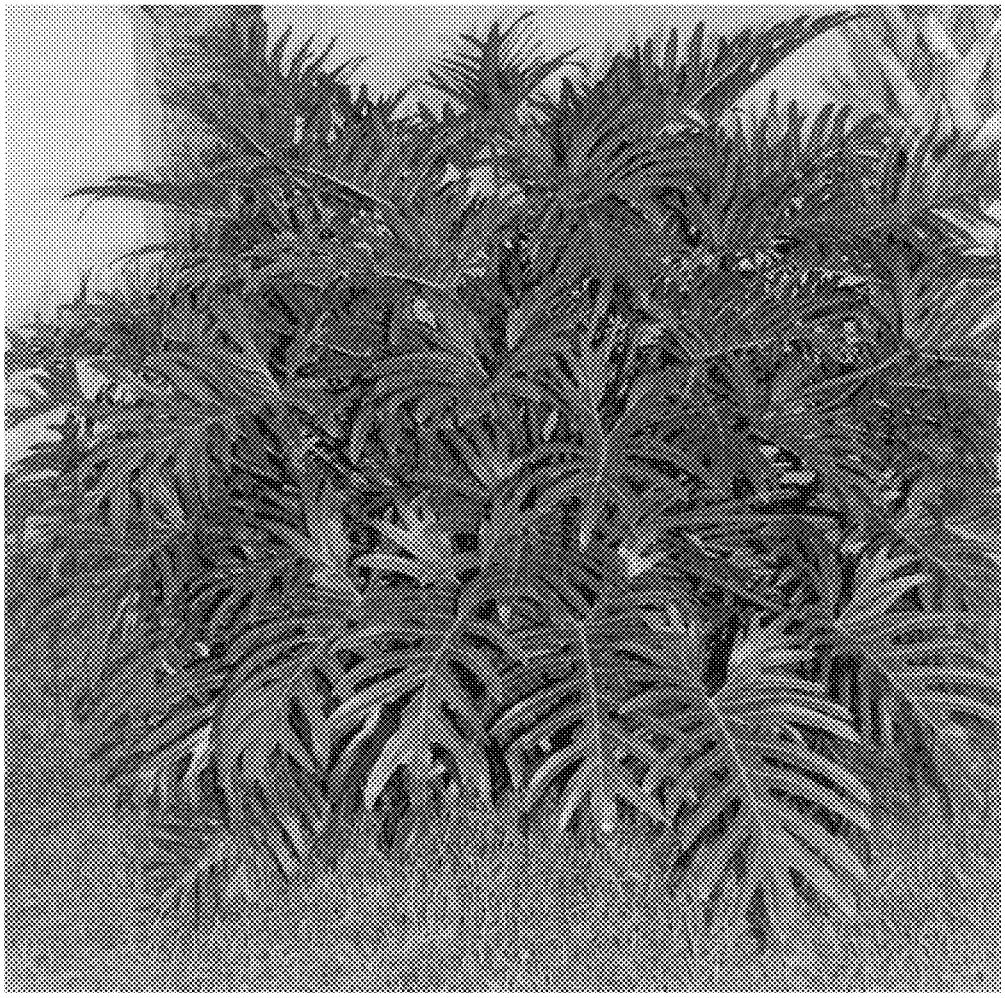

* * * * *